United States Patent [19]

Black et al.

[11] Patent Number: 4,973,246
[45] Date of Patent: Nov. 27, 1990

[54] DENTAL APPARATUS

[75] Inventors: John V. Black, Augusta, Ga.; Paul D. Sturges, Newberg, Oreg.

[73] Assignee: A-Dec, Inc., Newberg, Oreg.

[21] Appl. No.: 207,007

[22] Filed: Jun. 9, 1988

Related U.S. Application Data

[63] Continuation of Ser. No. 24,572, Mar. 11, 1987, abandoned.

[51] Int. Cl.$^5$ .............................................. A61C 3/00
[52] U.S. Cl. ..................................... 433/32; 433/80; 219/311
[58] Field of Search .................. 433/32, 80, 84, 85; 128/399, 400

[56] References Cited

U.S. PATENT DOCUMENTS

| | | | |
|---|---|---|---|
| 2,098,732 | 11/1937 | Prather | 433/32 |
| 2,420,338 | 5/1947 | Page | 433/84 |
| 4,026,025 | 5/1977 | Hunt | 433/80 |
| 4,108,178 | 8/1978 | Betush | 128/224 |
| 4,184,064 | 1/1980 | Williams | 219/303 |
| 4,302,185 | 11/1981 | Hall | 433/27 |
| 4,349,725 | 9/1982 | Sheridan | 219/373 |
| 4,531,913 | 7/1985 | Taguchi | 433/80 |
| 4,538,988 | 9/1985 | Henrichsen et al. | 433/84 |
| 4,759,712 | 7/1988 | Demand | 433/32 |

OTHER PUBLICATIONS

"A Short Course on Vortex Tubes and Application Notes" by Vortec Corporation (1974).
Ranque, G., "Experiments on Expansion in a Vortex with Simultaneous Exhaust of Hot Air and Cold Air", Le Journal de Physique et le Radium, Paris Review Bibliographique, Tome IV, Serie VII, Bulletin Bi-Mensuel, 2 Jun. 1933, p. 112S.

Primary Examiner—Gene Mancene
Assistant Examiner—Adriene B. Lepiane
Attorney, Agent, or Firm—Klarquist, Sparkman, Campbell, Leigh & Whinston

[57] ABSTRACT

A dental apparatus is provided which includes a handle having a hollow interior and an end portion which is slightly curved to facilitate insertion in the oral cavity of a dental patient. Within the hollow interior, an air heater system is provided consisting of an air vortex tube. Air is delivered to one end of the vortex tube in a direction perpendicular to the longitudinal axis of the tube causing the air to rapidly spin within the tube. The spinning air impinges upon an air flow control member at the opposite end of the tube which causes a portion of the air to deflect rearward toward its point of entry. This air is cool in temperature, and expelled from the rear of the tube. The non-deflected air is warm and directed out of the curved end portion of the handle. The invention further includes an adjustment system to control the temperature of air leaving the vortex tube.

18 Claims, 2 Drawing Sheets

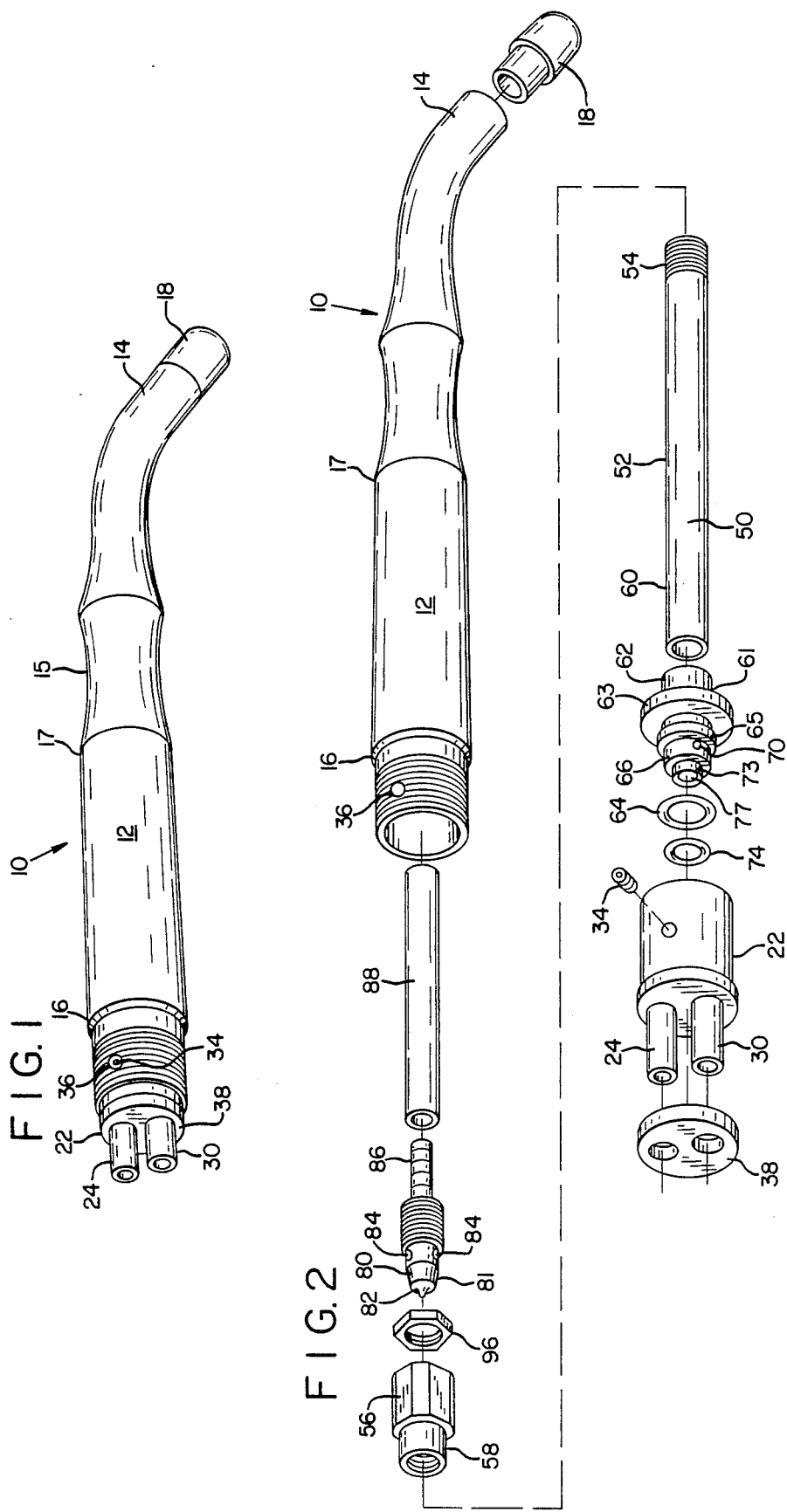

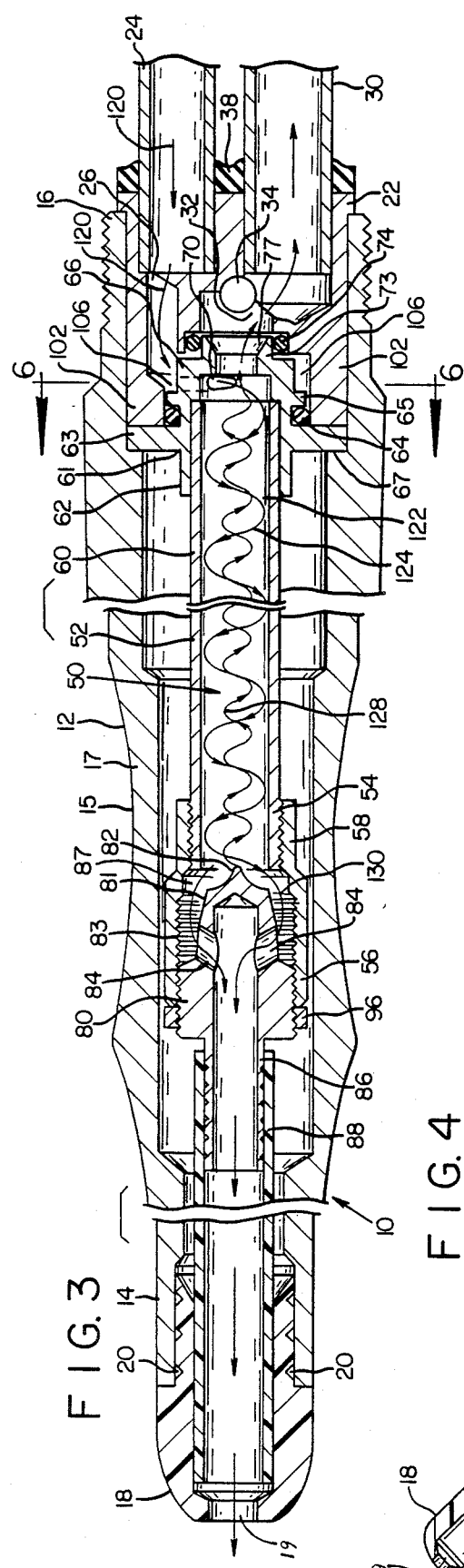
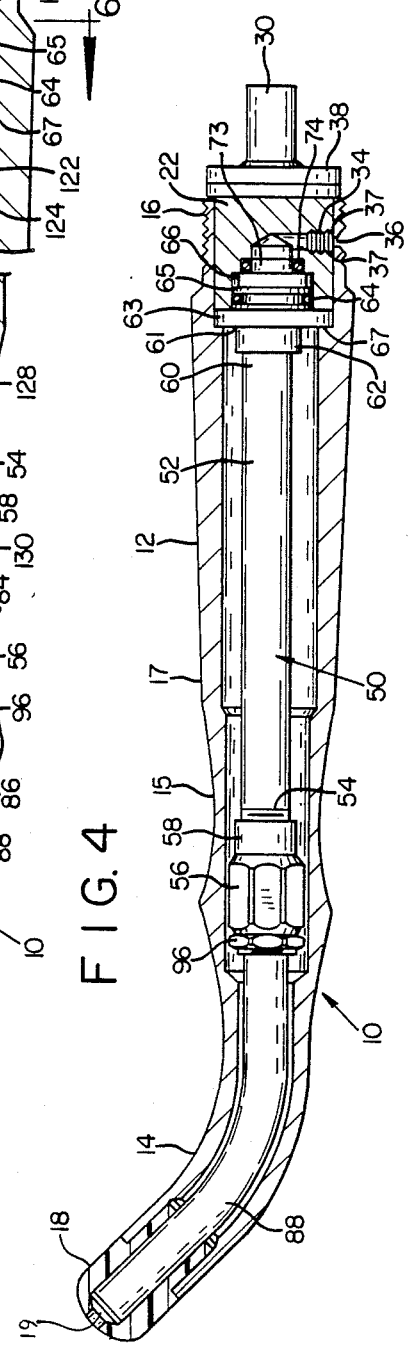
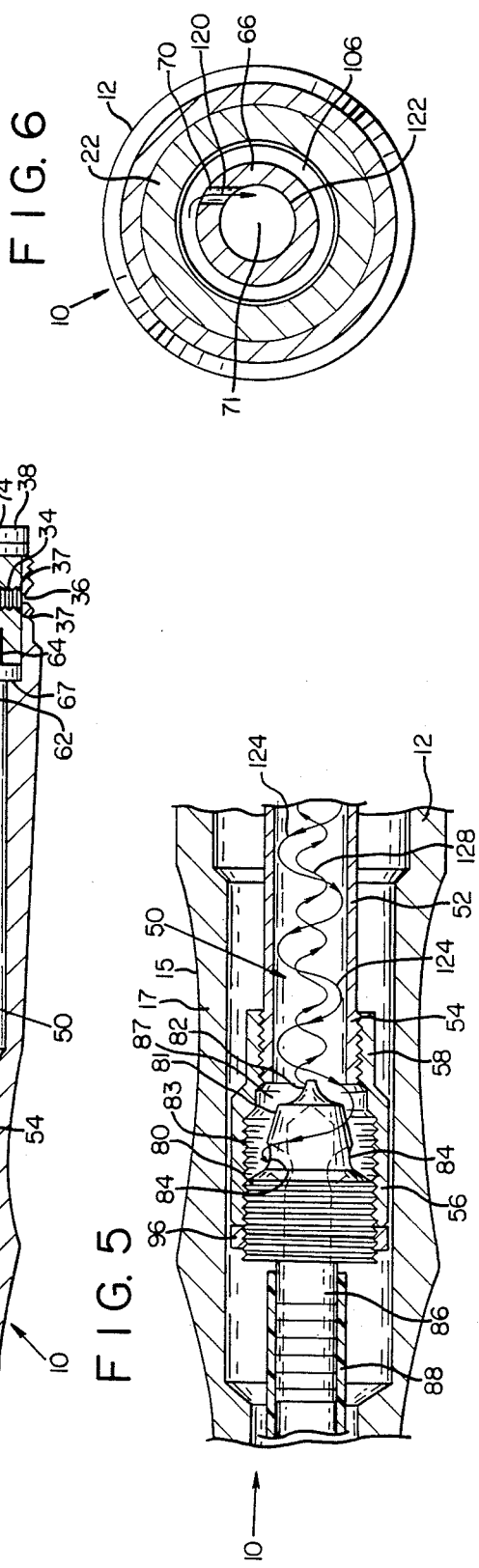

DENTAL APPARATUS

This application is a continuation, of application Ser. No. 024,572, filed Mar. 11, 1987, abandoned June 4, 1988.

BACKGROUND OF THE INVENTION

The present invention generally relates to a dental apparatus for delivering heated air to the oral cavity of a patient, and more particularly to a dental dryer having a self-contained, non-electrical system for internally generating and delivering heated air.

In most dental procedures, it is necessary to remove moisture from the tooth or regions of the mouth being treated. For example, when filling a decayed tooth, moisture must be removed from the tooth after drilling is completed and prior to the application of filling material. The failure to remove such moisture can result in an unstable, improperly constructed filling.

To accomplish the removal of moisture, dentists have applied heated air to the regions of the mouth being treated. This heated air is usually provided by instruments having air blower units. These instruments are often large, cumbersome, and require complex electrical heating systems.

For example, U.S. Pat. No. 2,420,338 to Page discloses a dental apparatus having a heated air blower. Pressurized air is supplied to the apparatus from an air source, and is delivered through an applicator. To heat the air, a complex system of electrical resistive heating elements is used.

Likewise, U.S. Pat. No. 4,026,025 to Hunt discloses a dental instrument for delivering pressurized water, air, or both to the oral cavity of a dental patient. The air is again heated using an electrical heating element.

The present invention represents a substantial departure from these and other dental instruments having air delivery systems. It is lightweight, easy to operate, and includes its own non-electrical, self-contained air heating system. These and other novel features of the invention will be described more fully below.

SUMMARY OF THE INVENTION

It is an object of the present invention to provide a dental apparatus with a heated air delivery system which is lightweight in construction, manufactured from inexpensive materials, and easy to operate.

It is another object of the present invention to provide a dental apparatus with a heated air delivery system which uses a minimal number of working components.

It is another object of the present invention to provide a dental apparatus with a heated air delivery system which is small and easily inserted within the oral cavity of a dental patient.

It is a still further object of the present invention to provide a dental apparatus with a heated air delivery system which is capable of delivering a constant and controlled supply of heated air to the oral cavity of a dental patient.

It is an even further object of the present invention to provide a dental apparatus with a heated air delivery system which incorporates an internal non-electric air heating system.

To accomplish these objectives, a dental apparatus with a heated air delivery system is provided which includes a handle having a hollow interior and an end portion which is slightly curved to facilitate insertion in the oral cavity of a dental patient. Within the hollow interior, a non-electrical air heating system is provided consisting of an air vortex tube. Air at ambient temperature is delivered to one end of the vortex tube at a direction perpendicular to the longitudinal axis of the tube. As a result, the air begins to rapidly spin and move down the tube. The spinning air contacts an air flow control member in the opposite end of the tube which causes a portion of the air to deflect back toward its original point of entry. This air is cool, and expelled from the rear of the apparatus. The non-deflected air is warm and passes out of the vortex tube through the curved end of the handle for application within the oral cavity of a dental patient The invention as described herein further includes an adjustment system to control the temperature of air leaving the vortex tube. As a result, air at a selectively warm temperature can be applied where needed in a fast and efficient manner while avoiding the use of complicated and expensive heating equipment.

These and other objects, features, and advantages of the invention will become apparent from the following drawings and detailed description of a preferred embodiment.

BRIEF DESCRIPTION OF THE DRAWINGS

FIG. 1 is a perspective view of a dental dryer constructed in accordance with the invention.

FIG. 2 is an exploded perspective view of the dryer of FIG. 1.

FIG. 3 is an enlarged, fragmentary cross sectional view of the dryer of FIG. 1.

FIG. 4 is a reduced scale partial cross sectional view showing the vortex tube assembly and other components within the outer sheath of the dryer.

FIG. 5 is a partial cross sectional view showing the arrangement of the air flow control member in the vortex tube of the dryer.

FIG. 6 is a sectional view taken along lines 6—6 of FIG. 1.

DETAILED DESCRIPTION OF A PREFERRED EMBODIMENT

The present invention represents an improved dental dryer for the delivery of heated air into the oral cavity of a dental patient. With reference to FIGS. 1, 2, and 4, the invention 10 includes a hollow handle 12 having a first or nozzle end 14, second or coupling end 16, and a medial portion 17. The handle 12 is preferably manufactured of aluminum or other metal capable of thermal sterilization and resistance to chemical agents normally encountered in dentistry.

The handle 12 becomes generally narrower in diameter from coupling end 16 to the nozzle end 14 as illustrated in FIGS. 1 and 4. The medial portion 17 includes a concave gripping region 15 which has a smooth surface to facilitate the cleaning and sterilization thereof. In addition, the nozzle end 14 is curved to facilitate its insertion into the mouth of a patient. The coupling end 16 is externally threaded for attachment to a standard four hole dental connector well known in the art, which includes air supply tubing and air exhaust tubing.

Secured to the nozzle end 14 is a rigid outlet tip 18 with a terminal opening 19. The tip 18 has a smooth surface to ensure safe insertion into a patient's mouth, and is preferably manufactured of a plastic material such as fluorocarbon plastic which is heat and chemical resistant fluorocarbon plastics also have low heat conductivity whereby the tip 18 will not become uncomfortably warm. As shown in FIGS. 3 and 4, the tip 18 is permanently bonded within the nozzle end 14 so that it will not fall out during use. To accomplish this, the tip 18 is glued into the nozzle end 14 using an adhesive material after both components have been thoroughly degreased. A preferred adhesive material is sold under the trademark Loctite 640 which is applied to both parts and subsequently cured for approximately 10 minutes at 200°–250° F.

To ensure proper adhesion between the tip 18 and nozzle end 14, the tip 18 includes a plurality of 60° V-grooves 20 which provide a reservoir for the adhesive material.

Seated in the coupling end 16 of the handle 12 is a cylindrical endpiece 22 shown in FIGS. 1–4. Attached to the endpiece 22 is an air intake conduit 24 which communicates with a bore 26 in endpiece 22 as illustrated in FIG. 3. Adjacent to and parallel with the air intake conduit 24 is an air exit conduit 30 which communicates with a central bore 32 in endpiece 22, also illustrated in FIG. 3. Both the air intake conduit 24 and air exit conduit 30 are secured to the endpiece 22 using a suitable adhesive such as Loctite 640.

The cylindrical endpiece 22 is maintained in position by a set screw 34 threaded radially into the endpiece 22. Access to the set screw 34 is provided through an opening 36 in the handle 12. The diameter of the set screw 34 is slightly larger than the diameter of the opening 36. After insertion of the endpiece 22 in the coupling end 16 with the set screw 34 fully withdrawn, a tool is inserted through opening 36 and set screw 34 is backed out so that it firmly engages the inside wall 37 of the handle 12 adjacent opening 36 (FIG. 4).

As previously noted, the coupling end 16 and conduits 24, 30 are adapted for attachment to a standard four hole dental connector well-known in the art (not shown). Secure and airtight attachment of the conduits 24, 30 to the aforesaid connector is facilitated through the use of a resilient elastomer gasket 38 shown in FIGS. 1–4.

Mounted in the medial portion 17 of the handle 12 is a vortex tube assembly 50 (FIGS. 2–4). Vortex tubes have been previously known and used in applications outside the dental field, primarily as a source of refrigerated air.

The vortex tube assembly 50 includes a tubular central conduit 52 having an externally threaded first end 54 threaded into the end 58 of a coupling member or adaptor 56 which is internally threaded (FIGS. 3 and 5). As illustrated in FIG. 4, the adaptor 56 is hexagonally shaped to minimize the contact and thermal conduction between the adaptor 56 and handle 12. The central conduit 52 also includes a second end 60 fitted to a vortex chamber element 61 designed for attachment to the endpiece 22. The element 61 is circular in cross section, and includes a connecting portion 62 which receives the central conduit 52 (FIG. 3). Adjacent the connecting portion 62 is an annular retaining flange 63 which abuts a step 67 formed on the inner periphery of the handle 12. Spaced longitudinally from the flange 63 is a rib 65 for maintaining in position an O-ring 64 which is used to form a seal between the endpiece 22 and the vortex chamber element 61. Adjacent rib 65 is an annular end portion 66 having an air inlet passageway 70 extending therethrough in a direction perpendicular to and laterally offset from the longitudinal axis 71 of the handle 12 (FIG. 6).

The vortex chamber element 61 further includes a terminal portion 73 having an O-ring 74. The O-rings 64, 74 ensure an airtight seal between the vortex chamber element 61 and endpiece 22. Extending through the terminal portion 73 is an air outlet passageway 77 in communication with the central conduit 52 of the vortex tube assembly 50 and the bore 32 of the endpiece 22.

Threaded into the adaptor 56 of the vortex tube assembly 50 is an air flow control member 80 having a substantially conical deflecting head including a frusto conical body portion 81 and a deflecting portion 82 comprising a substantially concave surface of revolution, as best shown in FIG. 5. The deflecting portion 82 extends into the end of the central conduit 50 and defines with such end an annular orifice 87. As will be evident, by adjusting the position of the air flow control member 80 axially with respect to the end of the conduit 50, the radial width of the orifice 87 can be adjusted. A pair of exit ports 84 extend through the frusto conical body portion 81 into the hollow interior thereof as illustrated in FIGS. 3 and 5. Attached to the end portion 86 of the air flow control member 80 is a tube 88 which is preferably manufactured of Teflon® fluorocarbon plastic or other material capable of resisting heat and chemical deterioration. Teflon® fluorocarbon plastic has a low heat conductivity which will prevent the loss of heat through the tube 88 from the flowing heated air. The tube 88 extends into and through the nozzle end 14 so as to provide a means for conducting heated air to the opening 19 in tip 18.

A lock nut 96 is threaded onto the air flow control member 80 and tightened against the adaptor 56 to lock the air flow control member 80 in position.

To assemble the invention 10, the vortex tube assembly 50 and attached air flow control member 80 are inserted into the handle 12 until the annular retaining flange 63 engages the step 67 formed in the handle 12 (FIG. 3). Next, the endpiece 22 and associated components are inserted into the coupling end 16 of the handle 12. Upon insertion, the set screw 34 is tightened against the interior wall 37 of the handle 12 as described above. The O-rings 64, 74 are compressed between the vortex chamber element 61 and the endpiece 22 as indicated in FIG. 3 so as to provide an airtight seal therebetween. This completes the assembly of the invention 10.

Once assembled, the end portions 102 of the endpiece 22 abut the annular retaining flange 63 as shown in FIG. 3. In this configuration, an air flow zone 106 is formed between the annular end portion 66 and the endpiece 22 (FIGS. 3 and 6). This enables air to flow from air intake conduit 24 through bore 26 into zone 106. Once in zone 106, the air enters air inlet passageway 70 and flows into the interior of the vortex tube assembly 50. This aspect of the invention 10 and its other functional features will be further explained in the following section entitled "Operation".

OPERATION

The conduits 24, 30 of the endpiece 22 are first attached to the standard four hole dental connector unit described above. Air at ambient temperature and a pressure of between 40–80 psi is introduced through air intake conduit 24. With reference to FIG. 3, the air flows through bore 26 in the endpiece 22 into zone 106 and through air inlet passageway 70 of the annular end portion 66. Air movement as described above is schematically illustrated in FIGS. 3 and 6 by arrows 120.

As shown in FIG. 6, the air moves down through air inlet passageway 70 in a direction perpendicular to the longitudinal axis 71 of the handle 12. After leaving passageway 70, the air strikes the interior surface 122 of the central conduit 52 of the vortex tube assembly 50 and begins to spin as a result of entering tangentially to the bore of conduit 52, as represented by arrows 124 in FIGS. 3 and 5. As the air spins, it expands and approaches sonic velocity. The velocity of spinning is such as to leave a low pressure zone or vacuum at the center of the conduit 52. The air continues to spin through the vortex tube assembly 50, and a portion thereof escapes through the annular orifice 87. The remaining air is deflected by the concave surface of the deflecting portion 82 into a smaller diameter vortex, illustrated by arrows 128 in FIGS. 3 and 5, and flows rearwardly through the low pressure zone toward the second end 60 of the central conduit 52 of the vortex tube assembly 50. This rearwardly flowing air undergoes loss of energy as its direction is reversed and its temperature decreases. The rearwardly flowing air then passes through air outlet passageway 77, bore 32, and out of the handle 12 through air exit conduit 30. Meanwhile, the air escaping through orifice 87 passes next through air exit ports 84 as illustrated by arrows 130 in FIG. 3. This air is heated and flows through end portion 86, tube 88, and out of the handle 12 through tip 18.

The aerodynamic principles behind the above-described generation of hot and cold air fractions are not precisely known. It is theorized that when the portion of air illustrated by arrows 128 strikes the air flow control member 80 and reverses direction, its linear velocity is reduced. Since kinetic energy is proportional to the square of linear velocity in a vortex tube system, kinetic energy will be lost by such air and transferred in the form of heat to the air passing over air flow control member 80 and out of the nozzle end 14.

Considerable air temperatures can be achieved using the present invention. For example, ambient air entering at a temperature of 70° F. and pressure of 80 psi can be heated to a temperature as high as 160° F.

The invention further includes means to control the temperature of the air leaving the tip 18. First, such temperature is proportional to the air inlet temperature and pressure. Increases in air inlet temperature and/or pressure will result in the production of warmer air. In the alternative, the temperature of the air discharged through the nozzle end 14 can be controlled by selective inward/outward adjustment of the air flow control member 80 with respect to the central conduit 52 of the vortex tube assembly 50. By loosening lock nut 96 and rotating air flow control member 80 outward, colder air will be produced. This occurs because as the radial width of the orifice 87 increases more of the colder centrally positioned gas portions will flow through the orifice together with the hot, peripherally positioned portions so that the blending will reduce the overall temperature of the gas discharged through the nozzle 14. The opposite effect is obtained when air flow control member 80 is rotated inward.

Having described herein a preferred embodiment of the present invention, it will be appreciated that suitable variations thereof may be made by those of ordinary skill in the art. Thus, it is intended that the scope of the present invention be construed according to the following claims.

I claim:

1. A dental apparatus for the generation and delivery of heated air to the oral cavity of a dental patient, comprising:

a handle having a first end, second end, and hollow medial portion therebetween;

inlet means in said second end for directing air from an external air source into said medial portion of said handle;

air vortex generator means within said medial portion of said handle for receiving said air from said inlet means and generating a heated air fraction and cooled air fraction therefrom;

first outlet means in said first end of said handle for receiving said heated air fraction from said vortex generator means and delivering said heated air fraction out of said handle to said oral cavity of said dental patient;

second outlet means in said second end of said handle adjacent said inlet means for directing said cooled air fraction out of said handle; said inlet means comprises an air intake conduit secured to an endpiece, said air intake conduit communicating with a first bore through said endpiece for directing air inwardly toward said vortex generator means, said endpiece being attached to said second end of said handle; said inlet means comprises an air intake conduit secured to an endpiece, said air intake conduit communicating with a first bore through said endpiece for directing air inwardly toward said vortex generator means, said endpiece being attached to said second end of said handle;

said vortex generator means comprising an air conduit having a first end, and a second end comprising an air inlet passageway for receiving air from said first bore in said end piece, said air inlet passageway extending through said second end in a direction perpendicular to the longitudinal axis of said handle, and an air flow control member mounted on said first end of said air conduit for deflecting a portion of air within said vortex generator means toward said second end thereof, said air portion representing said cooled air fraction, said air flow control member further comprising at least one opening therethrough through which a second portion of air not deflected by said air flow control member can pass, said second portion of air representing said heated air fraction, said air flow control member being threadably engaged with said first end of said vortex generator means so as to permit the movement of said air flow control member toward and outward relative to said air conduit to said vortex generator means to control the temperature of said heated air fraction, said outward movement of said air flow control member decreasing the temperature of said heated air fraction and said inward movement of said air flow control member increasing the temperature of said heated air fraction.

2. The dental apparatus of claim 1 further comprising locking means for maintaining said air flow control member in a selected position relative to said air conduit of said vortex generator means.

3. The dental apparatus of claim 1 wherein said first outlet means comprises an air delivery conduit within said handle and secured to said vortex generator means, said air delivery conduit being comprises of a heat insulating material.

4. The dental apparatus of claim 3 further comprising a tip secured to said first end of said handle and to said air delivery conduit, said tip being comprised of a heat insulating material.

5. The dental apparatus of claim 1 wherein said air flow control member comprises a frusto conical body portion, and an air deflecting portion adjacent said frusto conical body portion, said deflecting portion comprising a substantially concave surface of revolution, said opening in said air flow control member passing through said frusto conical body portion.

6. A dental apparatus for the generation and delivery of heated air to the oral cavity of a dental patient comprising:

a handle having a first end, a second end, and a hollow medial portion therebetween, said first end being curved so as to facilitate insertion thereof into the oral cavity of a dental patient;

inlet means at said second end for directing air from an external air source into said medial portion of said handle, said inlet means comprising an air intake conduit secured to an endpiece, said intake conduit communicating with a first bore through said endpiece for directing air into the medial portion of said handle, said endpiece being attached to said second end of said handle;

air vortex generator means within said medial portion of said handle for receiving said air from said inlet means and generating a heated air fraction and cooled air fraction therefrom, said vortex generator means comprising an air conduit having a first threaded end, and a second end comprising an air inlet passageway for receiving air from said first bore in said endpiece, said air inlet passageway extending through said second end in a direction perpendicular to the longitudinal axis of said handle, said second end of said vortex generator means further comprising an air outlet passageway extending therethrough in a direction perpendicular to that of said air inlet passageway in said second end;

first outlet means at said first end of said handle for receiving said heated air fraction from said vortex generator means and delivering said heated air fraction out of said handle to said oral cavity of said dental patient;

second outlet means in said second end of said handle for directing said cooled air fraction out of said handle, said second outlet means comprising an air exit conduit secured to said endpiece adjacent to and parallel with said air intake conduit, said air exit conduit communicating with a second bore in said endpiece, said second bore communicating with said air outlet passageway in said second end of said vortex generator means; and means within said vortex generator means for generating said heated air fraction and said cooled air fraction comprising an air flow control member at said first threaded end thereof for deflecting a portion of air within said vortex generator means toward said second end thereof, said portion representing said cooled air fraction, said air flow control member comprising a frusto conical body portion, and an air deflecting portion adjacent said frusto conical body portion, said deflecting portion having a substantially concave surface of revolution, said frusto conical body portion comprising at least one opening therethrough through which the portion of air not deflected by said deflecting portion can pass, said air representing said heated air fraction, said air flow control member being threadably engaged with said first threaded end of said vortex generator means so as to permit the movement of said air flow control member inward and outward relative to said air conduit of said vortex generator means to control the temperature of said heated air fraction, said outward movement of said air flow control member decreasing the temperature of said fraction, and said inward movement of said air flow control member increasing the temperature of said fraction.

7. Dental apparatus for the generation and delivery of heated air to the oral cavity of a dental patient comprising:

a handle having a first end, second end, and hollow medial portion therebetween;

inlet means in said second end for directing air from an external air source into said medial portion of said handle;

air vortex generator means within said medial portion of said handle for receiving said air from said inlet means and generating a heated air fraction and cooled air fraction therefrom, said vortex generator means comprising a movable air flow control member, the movement of said air flow control member changing the temperature of said heated air fraction;

first outlet means in said first end of said handle for receiving said heated air fraction from said vortex generator means and delivering said heated air fraction out of said handle to said oral cavity of said dental patient;

second outlet means in said second end of said handle adjacent said inlet means for directing said cooled air fraction out of said handle; and wherein said vortex generator means further comprises an air conduit having a first threaded end, and a second end, said air flow control member being threadably engaged with said first threaded end so as to permit the movement of said air flow control member inward and outward relative to said air conduit of said vortex generator means to control the temperature of said heated air fraction, said outward movement of said air flow control member decreasing the temperature of said fraction, and said inward movement of said air flow control member increasing the temperature of said fraction.

8. The dental apparatus of claim 7 wherein said first threaded end of said air conduit is hexagonal in cross section in order to minimize heat loss therethrough.

9. The dental apparatus of claim 7 further comprising locking means for maintaining said air flow control member in a selected position relative to said air conduit of said vortex generator means.

10. A dental apparatus for the generation and delivery of heated air to the oral cavity of a dental patient comprising:

a handle having a first end, a second end, and a hollow medial portion therebetween;

inlet means in said second end for directing air from an external air source into said medial portion of said handle;

outlet means for heated air in said first end; and air vortex generator means within said medial portion of said handle for receiving air from said inlet means and generating a heated air fraction and cooled air fraction therefrom, said vortex generator means comprising a tubular conduit and a flow control member mounted in one end of said conduit having a frusto conical body portion and an air deflecting portion adjacent said frusto conical body portion, said deflecting portion comprising a substantially concave surface of revolution, said frusto conical body portion comprising at least one opening therethrough communicating with said outlet means for conveying heated air thereto, said air flow control member mounted for axial movement relative to said conduit end.

11. The dental apparatus of claim 10 wherein said inlet means comprises an air intake conduit secured to an endpiece, said air intake conduit communicating with a first bore through said endpiece for directing air inwardly toward said vortex generator means, said endpiece being attached to said second end of said handle.

12. The dental apparatus of claim 11 further comprising:
second outlet means in said second end of said handle for directing said cooled air fraction out of said handle, said second outlet means comprising an air exit conduit secured to said endpiece adjacent to and parallel with said air intake conduit, said air exit conduit communicating with a second bore in said endpiece.

13. The dental apparatus of claim 12 wherein said vortex generator means comprises an air conduit having a first threaded end, and a second end comprising an air inlet passageway for receiving air from said first bore in said endpiece, said air inlet passageway extending through said second end in a direction perpendicular to the longitudinal axis of said handle.

14. The dental apparatus of claim 13 wherein said second end of said vortex generator means further comprises an air outlet passageway extending therethrough in a direction perpendicular to that of said air inlet passageway in said second end, said air outlet passageway communicating with second bore in said endpiece.

15. The dental apparatus of claim 14 wherein said second end of said vortex generator means further comprises retaining means for maintaining said vortex generator means in position within said medial portion of said handle, and sealing means for maintaining an airtight relationship between said second end of said vortex generator means and said endpiece.

16. The dental apparatus of claim 12 wherein said first end of said handle is curved so as to facilitate insertion thereof into the oral cavity of a dental patient.

17. The dental apparatus of claim 16 wherein said first end of said handle comprises a rigid plastic tip secured thereto.

18. A dental apparatus for the generation and delivery of heated air to the oral cavity of a dental patient comprising:
a handle having a first end, second end, and hollow medial portion therebetween;
inlet means in said second end for directing air from an external air source into said medial portion of said handle;
air vortex generator means within said medial portion of said handle for receiving said air from said air inlet means and generating a heated air fraction and cooled air fraction therefrom, said vortex generator means comprising an air conduit communicating with said air inlet means and an air flow control member, said air flow control member comprising a portion having a diameter less than that of said air conduit, said portion of said air flow control member extending into said air conduit so as to form an annular orifice therebetween;
means for adjusting the radial size of said annular orifice, said adjusting means regulating the temperature of the heated air fraction flowing through said orifice;
first outlet means in said first end of said handle for receiving the heated air fraction flowing through said orifice and delivering said heated air fraction out of said handle to said oral cavity of said dental patient;
second outlet means in said second end of said handle adjacent said inlet means for directing said cooled air fraction out of said handle; and
said air flow control member being threadably engaged with said air conduit so as to permit the inward and outward axial movement of said air flow control member relative to said air conduit, said outward movement of said air flow control member increasing the radial size of said annular orifice which decreases the temperature of the heated air fraction flowing therethrough, said inward movement of said air flow control member decreasing the radial size of said annular orifice which increases the temperature of the heated air fraction flowing therethrough.

* * * * *

UNITED STATES PATENT AND TRADEMARK OFFICE
CERTIFICATE OF CORRECTION

PATENT NO. : 4,973,246

DATED : November 27, 1990

INVENTOR(S) : John E. Black, et al

It is certified that error appears in the above-identified patent and that said Letters Patent is hereby corrected as shown below:

On the title page the following document titles were omitted from the list of "References Cited":

U.S PATENT DOCUMENTS

| | | |
|---|---|---|
| 3,074,243 | 1/22/63 | Tilden |
| 3,391,696 | 7/09/68 | Woodward |

Signed and Sealed this

Twenty-eighth Day of July, 1992

Attest:

DOUGLAS B. COMER

Attesting Officer     Acting Commissioner of Patents and Trademarks